United States Patent [19]

Mueller et al.

[11] Patent Number: 4,663,333
[45] Date of Patent: May 5, 1987

[54] ACYLAMINOALKYLPYRIDINES AD USE IN TREATMENT OF INFLAMMATION AND ALLERGY REACTIONS

[75] Inventors: Richard A. Mueller, Glencoe; Richard A. Partis, Evanston; James R. Deason, Wilmette, all of Ill.

[73] Assignee: G. D. Searle & Co., Skokie, Ill.

[21] Appl. No.: 809,955

[22] Filed: Dec. 20, 1985

[63] Continuation-in-part of Ser. No. 698,048, Feb. 4, 1985.

[51] Int. Cl.$^4$ .................. A61K 31/44; C07D 211/72; C07D 211/70
[52] U.S. Cl. .................. 514/346; 514/357; 546/291; 546/337
[58] Field of Search .................. 546/291, 334, 337; 514/346, 357

[56] References Cited

U.S. PATENT DOCUMENTS 3,931,200  1/1976  Gulbenk .................. 546/291

Primary Examiner—Henry R. Jiles
Assistant Examiner—Robert C. Whittenbaugh
Attorney, Agent, or Firm—S. M. Odre; R. E. L. Henderson; M. J. Kanady

[57] ABSTRACT

The compounds of this invention are acylaminoalkylpyridines representd by the formula

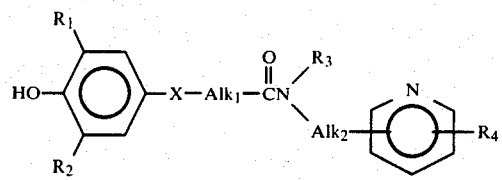

wherein: $R_1$ and $R_2$ are the same or different members of the group consisting of halo, phenyl, substituted phenyl and a

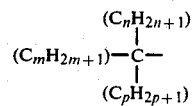

group wherein n, m and p are independently an integer of from 1 to 8 provided n+m+p is equal to or less than 10; X is thio, sulfinyl or sulfonyl; $Alk_1$ is straight or branched chain lower alkylene of 1 to 6 carbon atoms, $R_3$ is lower alkyl, $Alk_2$ is straight or branched chain alkylene of 1 to 4 carbon atoms; $R_4$ is selected from the group consisting of hydrogen, halo, hydroxy, lower alkyl and lower alkoxy; and the pharmaceutically acceptable salts thereof. The compounds of the present invention are useful in the treatment of inflammation, allergy and hypersensitivity reactions and other disorders of the immune system.

19 Claims, No Drawings

ACYLAMINOALKYLPYRIDINES AD USE IN TREATMENT OF INFLAMMATION AND ALLERGY REACTIONS

BACKGROUND OF THE INVENTION

A. Field of the Invention

This application is a continuation-in-part of application Ser. No. 698,048 filed Feb. 4, 1985.

The present invention relates to novel aminoalkylpyridineamides which are 5-lipoxygenase inhibitors and are useful as anti-inflammatory and anti-allergy agents.

It is well recognized that arachidonic acid and its analogs, unsaturated fatty acids, are the precursor of prostaglandins, thromboxanes, the 5-, 11-, 12- and 15-hydroxyeicosatetraenoic acids (HETEs, DIHETEs, TRIHETES) and hydroperoxyeicosatetraenoic acids (HPETEs) and the leukotrienes, all of which have profound physiological effects. The leukotrienes, which are produced via the 5-lipoxygenase pathway, are the major contributors to the onset of the symptoms of asthma, and mediators for immediate hypersenitivity reactions and inflammation.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other immediate hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, $D_5$ and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. The infiltration of eosinophils is one of the histologic features of a variety of allergic reactions.

With the exception of benoxaprofen, which has 5-lipoxygenase inhibition activity, aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid. These prostaglandin synthetase inhibitors generally exhibit anti-inflammatory, anti-pyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced pro-inflammatory effects. Administration of the NSAIDs alone can produce allergic reactions including bronchospastic reactivity; skin rashes; syndrome of abdominal pain, fever, chills, nausea and vomiting, and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs.

Prior to the recognition of the arachidonic acid cascade and the significance and interaction of the 5-lipoxygenase and other arachidonic acid cascade conversion products in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides acylaminoalkylpyridines which are metabolically stable inhibitors of the 5-lipoxygenase pathway and are useful in the treatment of asthma and other allergy and hypersensitivity reactions, and many types of inflammation.

To date, benoxaprofen has been the only commercial anti-inflammatory agent which has 5-lipoxygenase inhibition activity. Prior to its withdrawal from the market because of untoward side effects, benoxaprofen was considered to represent a significant advance in the treatment of crippling arthritis and psoriasis. Thus, there remains a longstanding need for agents which block the mechanisms responsible for inflammation and allergic reactions, and which can be safely employed to treat, for example, arthritis, asthma, psoriasis and other dermatoses, allergic reactions and other 5-lipoxygenase mediated conditions. A need also exists ffor agents which can be administered with the inhibitors of other lipoxygenase enzymes, e.g. cyclooxygenase, to mitigate their side effects and support their desirable medicinal properties.

See Bengt Samuelson, "Leukotrienes: Mediators of Immediate Hypersensitivity Reactions and Inflammation", *Science*, Vol. 220, pp. 568–575 (May 1983); Michael K. Bach, "Inhibitors of Leukotriene Synthesis and Action", *The Leukotrienes, Chemistry and Biology*, pp 163–194 (Academic Press, Inc., 1984); C. W. Lee et al., "Human Biology and Immunoreactivity of Leukotrienes", *Advances in Inflammation Research*, Volume 6, pp 219–225 (Raven Press, New York, 1984); Editorial, "Leukotrienes and other Lipoxygenase Products in the Pathegonesis and Therapy of Psoriasis and Dermatoses", *Arch. Dermatol.*, Vol. 119, pp 541–547 (July, 1983); Robert A. Lewis et al., "A Review of Recent Contributions on Biologically Active Prioducts of Arachidonate Conversion", *Int. J. Immunopharmac.*, Vol. 4, No. 2, pp 85–90 (1982); Michael K. Bach, *Biochemical Pharmacology*, Vol. 23, No. 4, pp 515–521 (1984); E. L. Becker, *Chemotactic Factors of Inflammation*, pp 223–225 (Eliver Science Publishers B. V., Amsterdam, 1983); P. Sharon and W. F. Stenson, *Gastroenterology*, Vol. 84, 454 (1984); and M. W. Musch, et al., *Science*, Vol. 217, 1255 (1982).

The present invention provides compounds which block the 5-lipoxygenase pathway of the arachidonic acid cascade, block the formation of the leukotrienes therefore responsible for the allergy and inflammation, and hence and represent a new class of therapuetic agents which are useful in the treatment of allergic and hypersenstivity reactions and inflammation, alone, or in combination with other oxygenase inhibitors such as the non-steroidal anti-inflammatory agents (cyclooxygenase inhibitors).

B. Prior Art

Wagner et al. U.S. Pat. No. 4,029,812, and related U.S. Pat. Nos. 4,076,841 and 4,078,084 which issued from divisional applications of the U.S. Pat. No. 4,029,812, all assigned to The Dow Chemical Company, disclose 2-(3,5-di-tert-butyl-4-hydroxyphenyl)thiocarboxylic acids, esters and simple amides which are hypolipidemics and are useful in reducing plasma lipid levels, especially cholesterol and triglyceride levels.

The Wagner et al. and related compounds have also been reported in the literature as plasticizers and pesticides. See for Example, *Izv. Vyssh. Uchebn. Zaved., Khim. Khim. Tekhnol.,* 20, 568–574 (1977); German Offenlegenschrift DE 2716125 (1977); *Pestic. Biochem. Physiol.* 1979, 12(1), 23–30. Chem. Abs. 90(19):151802x is of interest.

SUMMARY

The compounds of this invention are acylaminoalkylpyridines represented by the formula

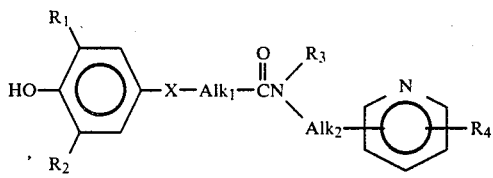

wherein: $R_1$ and $R_2$ are the same or different members of the group consisting of halo, phenyl, substituted phenyl and a

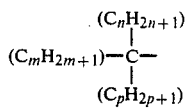

group wherein n, m and p are independently an integer of from 1 to 8 provided $n+m+p$ is equal to or less than 10; X is thio, sulfinyl or sulfonyl; $Alk_1$ is straight or branched chain lower alkylene of 1 to 6 carbon atoms; $R_3$ is lower alkyl; $Alk_2$ is straight or branched chain alkylene of 1 to 4 carbon atoms; $R_4$ is selected from the group consisting of hydrogen, halo, hydroxy, lower alkyl and lower alkoxy; and the pharmaceutically acceptable salts thereof.

The compounds of the present invention are useful in the treatment of allergy and hypersenitivity reactions and inflammation. The compounds are particularly useful in the treatment of arthritis and other inflammatory joint disease, asthma, proliferative skin disease such as psoriasis, and the like, alone or in combination with one or more cyclooxygenase inhibitors.

DETAILED DESCRIPTION OF PREFERRED EMBODIMENTS

The compounds of the present invention are generally administered in oral or parenteral dosages of from 0.1 to 100 mg/kg, preferably 0.5 to 50 mg/kg daily, preferably in divided dosages, to patients suffering from allergic or hypersensitivity reactions or inflammation, and are preferably applied topically to patients suffering from proliferative skin disease such as psoriasis. The compounds may be administered as the sole therapeutic agent, or in combination with other agents such as cyclooxygenase inhibitors, particularly in patients who exhibit pro-inflammatory or allergic response to, for example, conventional non-steroidal anti-inflammatory agents. Parenteral, e.g., intravenous, administration is preferable if a rapid response is desired, as, for example, in some cases of asthma.

Generally speaking, synthesis of the compounds of this invention is accomplished by displacement of the halogen or tosylate on a halo or tosyl substituted aliphatic acyl aminoalkylpyridine or substituted pyridine amide by a thiol in the presence of a base. Addition of a thiol to an unsaturated aliphatic acylaminoalkylpyridine amide is also an effective method of synthesis. Alternatively, the displacement, via reaction with a thiol and base, can be carried out on a tosyl or halo substituted aliphatic carboxylic acid or ester which is then converted into the final product via reaction of the corresponding acid chloride with the desired amine. The sulfones and sulfoxides are readily prepared by oxidation of the sulfides with, for example, m-chloroperbenzoic acid or sodium metaperiodate.

The term "lower alkyl", as used herein, refers to straight or branched chain alkyl groups having from 1 to 6 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The term "lower alkylene", as used herein, refers to straight or branched chain lower alkylene groups having from 1 to 6 carbon atoms, i.e., methylene, ethylene, n-propylene, iso-propylene, n-butylene, sec-butylene, tert-butylene, 3-methylpentylene, 2-methylbutylene, 1,1-dimethylethylene, and the like.

The term "substituted phenyl" refers to phenyl having one or more substituents selected from the group consisting of halo, hydroxy, lower alkyl and lower alkoxy.

The term "halo", as used herein, includes chloro, bromo, iodo and fluoro.

The term "lower alkoxy" refers to alkoxy groups having from 1 to 6 straight or branched chain carbon atoms, i.e., methoxy, propoxy, tert-butoxy, pentoxy etc.

Preferred radicals represented by the group of the formula

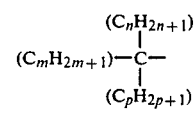

include tertiary alkyl moieties wherein n and m are preferably 1 or 2 and most preferred radical is represented by the group wherein n, m and p are 1, namely t-butyl.

The groups represented by X are preferably thio or sulfinyl and most preferably thio.

The term "pharmaceutically acceptable acid addition salts" refers to physiologically acceptable salts of the compounds of the present invention prepared by treating the compound with an appropriate acid as is well known in the art. Such salts include, but are not limited to, the hydrochloride, hydrobromide, sulfate, maleate, napsylate, oleate, succinate, palmitate, laurate, fumarate, phosphate, acetate, tartrate, stearate, nitrate, citrate, tosylate and like salts.

The selective activity of the compounds of this invention was first determined using the following assays.

Test A-An in vitro inhibition of soybean 15-lipoxygenase assay is employed to check the specificity of selected 5-lipoxygenase inhibitors. The oxygen-uptake during the oxidation of arachidonic acid to 15-HPETE by soybean lipoxygenase is measured in the presence and absence of inhibitors, using nordihydroguaiaretic acid (NDGA) as a reference standard. Compounds which inhibit at 100 μM are tested further to determine the IC$_{50}$ values. "IC" stands for "inhibitory concentration".

Test B-Determination of anti-inflammatory, anti-allergy activity: in vitro inhibition of 5-lipoxygenase. The 100,000 x g supernatant fraction of Rat Basophilic Leukemia Cell Homogenate (RBL-1) serves as a 5-lipoxygenase enzyme source. The enzyme is incubated with [1-$^{14}$C]-arachidonic acid and Ca$^{++}$ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the IC$_{50}$ value.

Test C-Inhibition of slow reacting substance (SRS) biosynthesis in cells. SRS synthesis by Rat Basophilic Leukemia Cell (RBL-1) cells is induced by incubation of cells with ionophore A23187 alone and in combination with the test compound. The SRS released into the culture media is measured by high pressure liquid chromatography, scintillation counting or bioassay. In the bioassay procedure, the percent inhibition of SRS production is estimated by determining the doses of treated and control media needed in the tissue bath to produce equivalent contractions of segments of isolated guinea pig ileum. A compound that inhibits SRS biosynthesis by 50% or more is considered active at that concentration if an equivalent amount of the compound does not antagonize ileum contraction by SRS directly. If the compound directly inhibits the smooth muscle contractions, it will be considered inactive as an SRS biosynthesis inhibitor. Initial screening doses of test compounds are $1 \times 10^{-4}$M and $1 \times 10^{-5}$M.

Test-D-In vitro inhibition of human platelet 12-lipoxygenase. A 40,000×g supernatant of platelet lysate is incubated with [1-$^{14}$C]-labeled arachidonic acid in the presence and absence of test compound. The conversion product, 12-hydroxyeicosatetraenoic acid (12-HETE), is quantitated after isolation by thin-layer chromatography. Compounds, initially screened at 100 μM concentration, which inhibit the synthesis of 12-HETE by 30% or more, are considered active. IC$_{50}$ values are determined for active compounds.

Test E-In vitro inhibition of sheep seminal vesicle microsome cyclooxygenase. Arachidonic acid cyclooxygenase reaction rates, in the presence or absence of test compounds, are determined by monitoring oxygen uptake. Compounds which inhibit at $10^{-4}$M are tested further to determine IC$_{50}$ values.

The following examples further illustrate the present invention.

EXAMPLE 1

Preparation of 3,5-bis(1,1-dimethylethyl)-4-hydroxyphenylthiocyanate

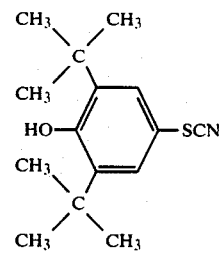

To a three-necked, round bottom 5 L flask, equipped with a mechanical stirrer, gas inlet, thermometer and gas inlet, thermometer and gas outlet, was added 2,6-di-tert-butylphenol (474 g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1½ hours, maintaining the reaction mixture at a temperature of between 0° to 10° C. The reaction was stirred for an additional hour at 0° C., poured into a 2 L of cold distilled water and refrigerated overnight. The aqueous phase was decanted and the solid taken up in methanol, precipitated from water, filtered and dried for 2 days over phosphorous pentoxide. The resulting gummy yellow solid was recrystallized from pentane and dried in vacuo to yield the product as a white powder, m.p. 61.5°-63° C.

Analysis calc. for C$_{15}$H$_{21}$NSO: Theory: C, 68.40; H, 8.03; N, 5.32; S, 12.17. Found: C, 68.85; H, 8.05; N, 5.29; S, 12.12.

EXAMPLE 2

Preparation of 2,6-bis(1,1-dimethylethyl)-4-mercaptophenol

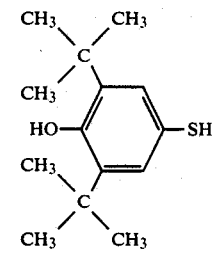

3,5-bis(1,1-Dimethylethyl)-4-hydroxyphenyl thiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the identity of the product.

EXAMPLE 3

Preparation of
N-methyl-N-[2-(2-pyridinyl)ethyl]-2-propenamide

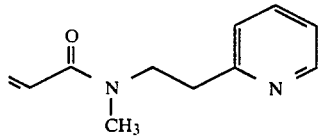

Acryloyl chloride (4.52 g, 0.05 mole) was added dropwise to a stirring solution of triethylamine (30 ml) and 2-(β-methylaminoethyl)pyridine (6.81 g, 0.05 mole) in ethyl ether (500 ml). After stirring overnight at room temperature, the white solid was removed by filtration and washed well with ethyl ether. The organic phases were combined, dried over sodium sulfate, filtered then concentrated to dryness to give an orange oil. The structure was confirmed by NMR.

EXAMPLE 4

Preparation of
3-[[3,5-bis(1,1-dimethylethyl)-4-hydroxyphenyl]thio]-
N-methyl-N-[2-(2-pyridinyl)ethyl]propanamide

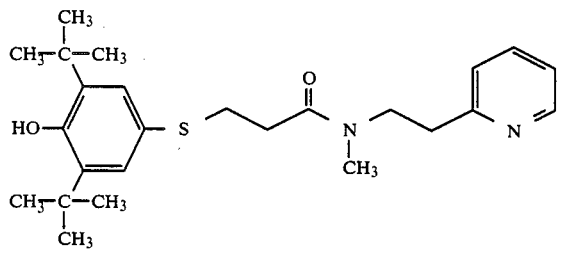

N-methyl-N-[2-(2-pyridinyl)ethyl]-2-propenamide (0.95 g, 0.005 mole) was dissolved in methanol (200 ml) containing 2,6-bis(1,1-dimethylethyl)-4-mercaptophenol (1.19 g, 0.005 mole). After addition of triethylamine (0.5 ml), the solution was stirred at room temperature overnight. The solvent was removed by a nitrogen stream to give a residue which was purified by chromatography on silica to give the title compound, m.p. ca. 82°–84° C.

Anal. calcd. for $C_{25}H_{36}N_2O_2S$(428.62): Calc.: C, 70.05; H, 8.47; N, 6.54; S, 7.47. Found: C, 70.45; H, 8.50; N, 6.60; S, 7.55.

EXAMPLE 5

Preparation of
3-[[3,5-bis(1,1-dimethylethyl)-4-hydroxyphenyl]thio]-
N-methyl-N-[2-(2-pyridinyl)ethyl]propanamide
monohydrochloride

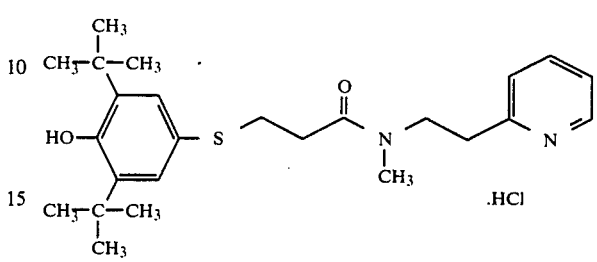

The title compound of Example 4, (2.0 g) was dissolved in ethyl ether (400 ml). With rapid stirring, a saturated solution of hydrogen chloride in isopropyl alcohol was added dropwise until no further precipitation occurred. The oily material was stirred for 20 hours. The ethyl ether was decanted and the residue crystallized from ethyl acetate/ethyl ether to give the title compound (700 mg), m.p. ca. 153°–156° C.

Analysis calc for $C_{25}H_{37}N_2SOCl$(465.09): Calc.: C, 64.56; H, 8.02; N, 6.02; Cl, 7.62; S, 6.89. Found: C, 64.30; H, 7.88; N, 6.00; Cl, 7.79; S, 6.91.

EXAMPLE 6

Preparation of
N-ethyl-N-(4-pyridinylmethyl)-2-propenamide

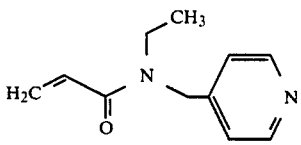

Following the method of Example 3, 4-picolylethylamine (4.27 g, 0.035 mole) was reacted with acryloyl chloride (3.15 g, 0.035 mole) was triethylamine (21 ml) and purified by chromatography on silica.

Analysis calc. for $C_8H_{12}N_2$(136.20): Calc.: C, 69.44; H, 7.92; N, 14.72. Found: C, 69.26; H, 7.56; N, 14.59.

EXAMPLE 7

Preparation of
3-[[3,5-bis(1,1-dimethylethyl)-4-hydroxyphenyl]thio]-
N-ethyl-N-(4-pyridinylmethyl)propanamide

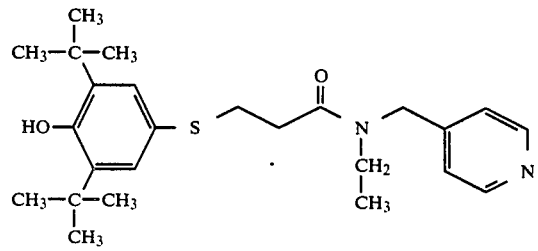

The title compound was prepared according to the method of Example 4 from N-ethyl-N-(4-pyridinylmethyl)-2-propenamide (1.5 g, 0.00788 mole,), 2,6-bis(1,1-dimethyl-ethyl)-4-mercaptophenol (2.06 g, 0.00867 mole,) and triethylamine (1 ml) to provide 3.0 g of product, m.p. ca. 121°–123° C.

Analysis calc. for $C_{25}H_{36}N_2O_2S(428.63)$: Calc.: C, 70.05; H, 8.47; N, 6.54; S, 7.48. Found: C, 70.23; H, 8.55; N, 6.34; S, 7.55.

EXAMPLE 8

Preparation of N-methyl-N-[(2-methyl-6-pyridinyl)methyl]-2-propenamide

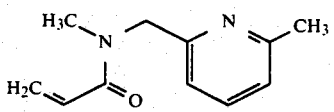

The title compound was prepared according to the method of Example 6 from 6-methyl-2-picolylmethylamine (4.27 g, 0.035 mole), acryloyl chloride (3.15 g, 0.035 mole) and triethylamine (21 ml) in methylene chloride.

Analysis calc. for $C_{11}H_{14}N_2O(190.24)$: Calc.: C, 69.44; H, 7.42; N, 14.72. Found: C, 69.41; H, 7.53; N, 14.68.

EXAMPLE 9

Preparation of 3-[[3,5-bis(1,1-dimethylethyl)-4-hydroxyphenyl]thio]-N-methyl-N-[(2-methyl-6-pyridinyl)methyl]propanamide

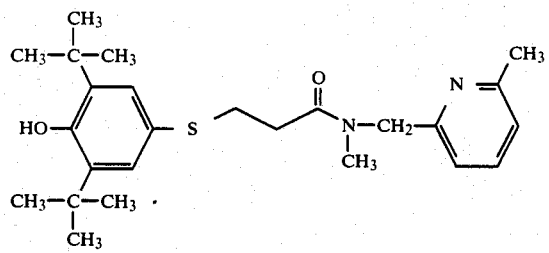

The title compound was prepared according to the method of Example 4 from the amide of Example 8 (1.9 g, 0.01 mole), the thiol of Example 4 (2.38 g, 0.01 mole) and triethylamine (1 ml) in methanol to provide 3.95 g of product.

Analysis calc. for $C_{25}H_{36}N_2O_2S(428.63)$: Calc.: C, 70.05; H, 8.47; N, 6.54; S, 7.48. Found: C, 69.80; H, 8.59; N, 6.32; S, 7.57.

EXAMPLE 10

Preparation of N-methyl-N-[2-(4-pyridinyl)ethyl]-2-propenamide

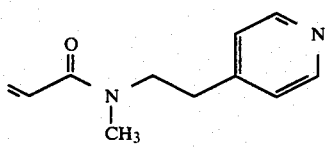

The title compound was prepared according to the method of Example 3 from 4-[β-(methylamino)ethyl]pyridine (4.76 g, 0.035 mole), acryloyl chloride (3.15 g, 0.035 mole) and triethylamine (21 ml) to yield 3.4 g of product, m.p. ca. 129°–132° C.

Analysis calc. for $C_{11}H_{14}N_2O(190.24)$: Calc.: C, 69.45; H, 7.42; N, 14.72. Found: C, 69.79; H, 7.62; N, 14.20

EXAMPLE 11

Preparation of 3-[[3,5-bis(1,1-dimethylethyl)-4-hydroxyphenyl]thio]-N-methyl-N-[2-(4-pyridinyl)ethyl]propanamide

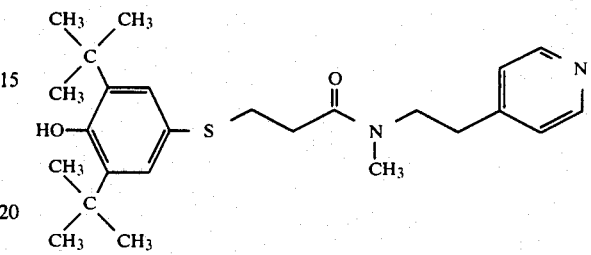

The title compound was prepared according to the method of Example 4 from the thiol of Example 2 (2.61 g, 0.011), the amide of Example 10 (1.9 g, 0.010 mole) and triethylamine (1 ml) to yield 3.4 g of product, m.p. ca. 129°–131.5° C.

Analysis calcd. for $C_{25}H_{36}N_2O_2S(428.63)$: Calcd. C, 70.05; H, 8.47; N, 6.53; S, 7.48. Found: C, 70.15; H, 8.58; N, 6.47; S, 7.71.

EXAMPLE 12

Preparation 3,5-dichloro-4-hydroxyphenyl thiocyanate

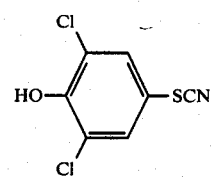

2,6-Dichlorophenol (100 g, 0.613 mole) and ammonium thiocyanate (102.73 g, 1.350 mole) were mixed in methanol and the solution cooled to 0° C. Chlorine gas was bubbled through the reaction, maintaining the temperature below 10° C. The solution turned a pale yellow color. The reaction was stirred for a total of 3 hours until acidic, at which time ammonia gas was bubbled through and the solution stirred for an additional three hours at 0° to 10° C. The reaction was poured into iced distilled water, and filtered, yielding approximately 20 g of a yellow solid which was dried overnight in vacuo. The filtrate was extracted with ethyl acetate, dried over magnesium sulfate and stripped to yield approximately 100 g of crude product. Following purification by chromatography, the material was taken up to 1 liter of toluene, charcoal added, filtered and recrystallized from hexane to yield 55.03 g of prioduct as a yellow solid. The structure was confirmed by NMR.

EXAMPLE 13

Preparation of 2,6-dichloro-4-mercaptophenol

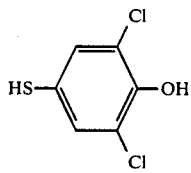

The title compound of Example 12 (55.03 g, 0.25 mole) was dissolved in 300 ml of acetone. Water (9 ml), was added and the solution cooled to 0° C. Treithylphosphine (36.9 ml, 0.250 mole) was added dropwise over a period of 65 minutes, maintaining the temperature at 0° C. The reaction was allowed to warm to room temperature, stirred for 1½ hours, the solvent was removed and the product purified by chromatography and recrystallized from hexane to give the title compound.

Analysis Calcd. for $C_6H_4OCl_2S$ (195.08): Calcd.: C, 36.94; H, 2.07; Cl, 36.35; S, 16.44. Found: C, 36.96; H, 2.06; Cl, 36.31; S, 16.56.

EXAMPLE 14

Preparation of
3-[(3,5-dichloro-4-hydroxyphenyl)thio]-N-methyl-N-[2-(2-pyridinyl)ethyl]propanamide

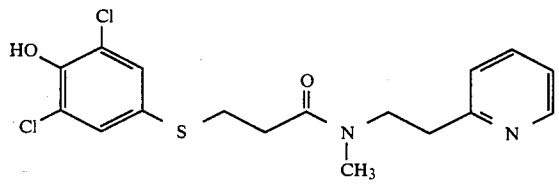

The title compound was prepared according to the method of Example 4, from N-methyl-N-[2-(2-pyridinyl)ethyl]-2-propenamide (2.5 g. 0.013 mole), 2,6-dichloro-4-mercaptophenol (2.56 g, 0.013 mole) and triethylamine (5 ml), m.p. about 120°–123° C.

Analysis calc. for $C_{17}H_{18}N_2O_2Cl_2S$ (385.31): Calc.: C, 52.97; H, 4.71; N, 7.27; Cl, 18.40; S, 8.32. Found: C, 53.18; H, 4.89; N, 7.34; Cl, 18.59; S, 8.05.

EXAMPLE 15

Preparation of 2'-hydroxy[1,1':3',1''-terphenyl]-5'-yl thiocyanate

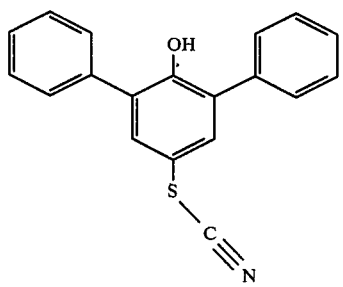

2,6-Diphenylphenol (100.0 g, 0.406 mole) and ammonium thiocyanate (67.99 g, 0.893 mole) were suspended in methanol (150 ml) in a three-necked round bottom flask equipped with magnetic stirrer, thermometer and bubbler. The reaction mixture was cooled to −5° C. in an acetone/ice bath and chlorine gas bubbled through the solution for three hours. Maintaining the temperature below 10° C., ammonia gas was bubbled through the reaction for 2 hours. The contents of the flask were then poured into iced distilled water and allowed to stand for 12 hours in the refrigerator. After filtering, the solid was dried in vacuo at 45° C. for 12 hours. The title compound was purified by chromatography and recrystallized from hexane, m.p. about 104°–106.5° C.

Analysis calc. for $C_{19}H_{13}OSN$ (303.39): Calc.: C, 75.22; H, 4.32; N, 4.62; S, 10.57. Found: C, 75.12; H, 4.49; N, 4.65; S, 10.41.

EXAMPLE 16

Preparation of 5'-mercapto[1,1':3',1''-terphenyl]-2'-ol

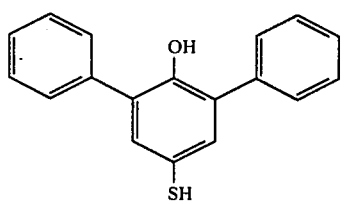

The title compound of Example 15 (32.2 g, 0.106 mole) and water (1.9 ml) were dissolved in acetone (150 ml) with stirring and cooled to −5° C. Triethylphosphine (15.7 ml, 0.106 mole) was added dropwise over a period of 40 minutes. The reaction was stirred at 0° C. for 1 hour and then at room temperature for 2 hours. The solvent was evaporated and the product isolated by chromatography on silica.

Analysis Calcd. for $C_{18}H_{14}OS$ (278.31): Calcd.: C, 77.67; H, 5.07; S, 11.52. Found: C, 77.80; H, 5.19; S, 11.68.

EXAMPLE 17

Preparation of
3-[(2'-hydroxy[1,1':3',1''-terphenyl]-5'-yl)-thio]-N-methyl-N-[2-(2-pyridinyl)ethyl]propanamide

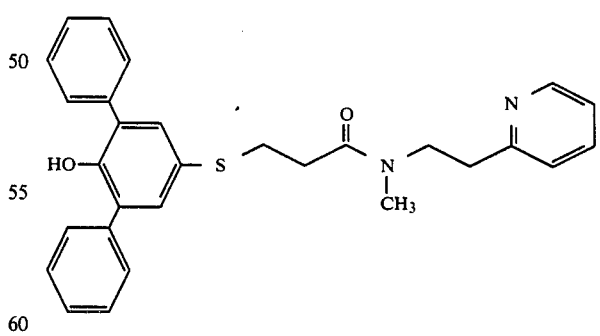

The title compound was prepared according to the method of Example 4 from the thiol of Example 16 (2.78 g, 0.01 mole), N-methyl-N-[2-(2-pyridinyl)ethyl]-2-propenamide (1.90 g, 0.01 mold) and triethylamine (1.2 ml).

Analysis calc. for $C_{29}H_{28}O_2N_2S$ (468.54): Calc.: C, 74.32; H, 6.02; N, 5.98. Found: C, 73.93; H, 6.04; N, 6.16.

EXAMPLE 19

Preparation of 4-[[3,5-bis(1,1-dimethylethyl)-4-hydroxy phenyl]thio]butanoic acid

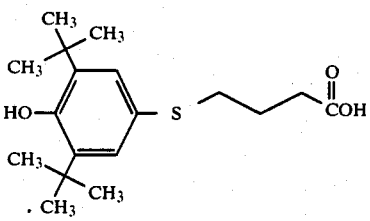

Potassium hydroxide flakes (2.52 g, 0.045 mole) were added to a clear solution of 2,6-bis(1,1-dimethylethyl)-4-mercaptophenol (3.57 g, 0.015 mole) and ethyl-4-bromobutyrate (3.23 g, 0.0165 mole) in acetone (10 ml). Water (20 ml) was added and the solution stirred for 1.5 hours, the solvent removed on a rotary evaporator and water (50 ml) added. The organic layer was extracted with ethyl ether (3×75 ml). The aqueous layer was acidified with concentrated hydrochloric acid, extracted with ethyl ether (2×50 ml), washed with water (50 ml), dried over sodium sulfate, filtered and the solvents removed, leaving an oil, which was purified by chromatography on silica, recrystallized from ethyl ether/Skellysolve B, filtered and the product dried in vacuo at room temperature for 12 hours, m.p. ca. 112°–113.5° C.

Analysis calc. for $C_{18}H_{28}O_3S$(324.48): Calc.: C, 66.63; H, 8.70; S, 9.88. Found: C, 66.71; H, 8.74; S, 9.57.

EXAMPLE 19

Preparation of 4-[4-[3,5-bis(1,1-dimethylethyl)-4-hydroxyphenyl]thio]-N-methyl-N-[2-(2-pyridinyl)ethyl]butanamide

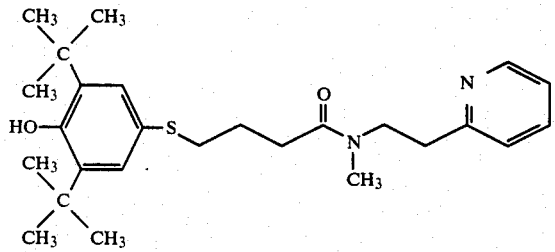

The title comound of Example 18 is dissolved in benzene and the solution cooled to about 5° C. in an ice bath. A solution of oxalyl chloride in benzene is added dropwise over a period of about 5 minutes. The ice bath is removed and the solution is allowed to warm to room temperature and is stirred for about 5 hours. The benzene is evaporated and fresh benzene is added. Triethylamine and 2-(β-methylaminoethyl)pyridine are added and the solution is stirred overnight. The benzene is evaporated on a rotary evaporator and the product is purified by chromotagraphy on silica.

EXAMPLES 20–22

By replacing 2,6-bis(1,1-dimethylethyl)-4-mercaptophenol with 2,6-dichloro-4-mercaptophenol in the procedures of Examples 7, 9, and 11, the following compounds are obtained.

Example 20. 3-[(3,5-dichloro-4-hydroxyphenyl)thio]-N-ethyl-N-(4-pyridinylmethyl)propanamide.

Example 21. 3-[(3,5-dichloro-4-hydroxyphenyl)thio]-N-methyl-N[(2-methyl-6-pyridinyl)methyl]propanamide.

Example 22. 3-[(3,5-dichloro-4-hydroxyphenyl)-thio]-N-methyl-N-[2-(4-pyridinyl)ethyl]propanamide.

EXAMPLES 23–25

By replacing 2,6-bis(1,1-dimethylethyl)-4-mercaptophenol with 5'-mercapto[1,1':3',1''-terphenyl]-2'-ol in the procedures of Examples 7, 9 and 11, the following compounds are obtained.

Example 23. 3-[(2'-hydroxy[1,1':3',1''-terphenyl]-5'-yl)thio]-N-ethyl-N-(4-pyridinylmethyl)propanamide.

Example 24. 3-[(2'-hydroxy(1,1':3',1''-terphenyl]-5'-yl)thio]-N-methyl-N-[(2-methyl-6-pyridinyl)methyl]-propanamide.

Example 25. 3-[(2'-hydroxy[1,1':3',1''-terphenyl]-5'-yl)thio]-N-methyl-N-[2-(4-pyridinyl)ethyl]propanamide.

EXAMPLES 26–32

By substituting the appropriate alkylpyridyl amide for the starting amides of Examples 4, 7, 9, 11, etc., the following representative products are obtained.

Example 26. 4-[(2'-hydroxy[1,1':3',1''-terphenyl]-5'-yl)thio]-N-methyl-N-[2-(2-pyridinyl)ethyl]butanamide, Example 27. 2-[(3,5-dichloro-4-hydroxyphenyl)thio]-N-ethyl-N-(4-pyridinylmethyl)-acetamide.

Example 28. 2-[(3,5-dichloro-4-hydroxyphenyl)-thio]-N-methyl-N-[(2-methyl-6-pyridinyl)methyl]ethanamide.

Example 29. 3-[(3,5-dichloro-4-hydroxyphenyl)-thio]-N-methyl-N-[2-(2-pyridinyl)ethyl]-iso-propanamide.

Example 30. 4-[(3,5-bis(1,1-dimethylethyl)-4-hydroxyphenyl]thio]-N-methyl-N-[2-(2-pyridinyl)ethyl]-2,2-dimethylbutamamide.

Example 31. 2-[(2'-hydroxyl[1,1':3',1''-terphenyl]-5'-yl)thio]-N-methyl-N-[2-(4-pyridinyl)ethyl]pentanamide.

Example 32. 2-[(2'-hydroxyl[1,1':3',1''-terphenyl]-5'-yl)thio]-N-methyl-N-[2-(4-pyridinyl)ethyl]hexanamide.

The active agents of this invention can be administered to animals, including humans, as pure compounds. However, it is advisable to first combine one or more of the active compounds with one or more suitable pharmaceutically acceptable carriers or diluents to attain a satisfactory size to dosage relationship and thereby obtain a pharmaceutical composition.

Pharmaceutical carriers which are liquid or solid can be employed. Solid carriers such as starch, sugars, talc and the like can be used to form powders which may be used for direct administration or to fill gelatin capsules. Suitable lubricants such as magnesium stearate, stearic acid, as well as binders and disintegrating agents may be included to form tablets. Additionally, flavoring and sweetening agents may be added.

Unit dosage forms such as tablets and capsules can contain any suitable, predeterined, therapeutically effective amount of one or more active agents and a pharmaceutically acceptable carrier or diluent. Generally speaking, solid oral unit dosage forms of a compound of this invention will contain from 1.75 to 750 mg per tablet of drug.

The compounds of this invention exhibit both oral and parenteral activity and accordingly can be formulated in dosage forms for either oral or parenteral administration.

Solid oral dosage forms include capsules, tablets, pills, powders, granules and the like.

Liquid dosage forms for oral administration include emulsions, suspensions, solutions, syrups and the like containing diluents commonly used in the art such as water. Besides inert diluents, such preparations can also include adjuvants such as wetting agents, emulsifying and suspending agents, and sweetening, flavoring and perfuming agents.

Preparations for parenteral administration include sterile aqueous or non-aqueous solutions. Examples of nonaqueous solvents or vehicles are propylene glycol, polyethylene glycol, vegetable oils such as olive oil and injectable organic esters such as ethyl oleate. The parenteral preparations are sterilized by conventional methods.

The compounds of this invention may also be formulated for topical or transdermal application using carriers which are well known in the art, as well as in aerosols or sprays for nasal administration.

The amount of active ingredient administered may be varied; however, it is necessary that the amount of active ingredient be such that a suitable dosage is given. The selected dosage depends upon the desired therapeutic effect, the route of administration and the duration of treatment. Generally speaking, oral dosages of from 0.1 to 100 mg/kg, and preferably from 0.5 to 50 mg/kg of body weight daily are administered to patients in need of such treatment, preferably in divided dosages, e.g. three to four times daily. In the case of acute allergic or hypersensitivity reactions, it is generally preferable to administer the initial dosage via the parenteral route, e.g. intravenous, and continue parenteral administration until the patient is stabilized, and can be maintained, if necessary on oral dosing.

In the case of psoriasis and other skin conditions, it is preferred to apply a topical preparation of a compound of this invention to the affected areas three or four times daily.

In treating asthma and arthritis with a compound of this invention, the compounds may be administered either on a chronic basis, or as symptoms appear. However, in the case of arthritis and other inflammatory conditions which can lead to deterioration of joints and malformations, it is generally preferable to administer the active agents on a chronic basis.

When the compounds of this invention are co-administered with one or more cyclooxygenase inhibitors, they may conveniently be administered in a unit dosage form or may be administered separately. When the patient is allergic or hypersensitive to the cycloxygenase inhibitor, it is preferred to initiate therapy with a compound of this invention prior to administration of the cyclooxygenase inhibitor.

A typical tablet of this invention can have the following composition:

| Ingredient | mg/tablet |
| --- | --- |
| Active ingredient | 100 |
| Starch, U.S.P. | 57 |
| Lactose, U.S.P. | 73 |
| Talc, U.S.P. | 9 |
| Stearic acid | 12 |

It will be understood by those skilled in the art that the above examples are illustrative, not exhaustive, and that modifications may be made without departing from the spirit of the invention and the scope of the claims.

The invention claimed is:

1. A compound of the formula

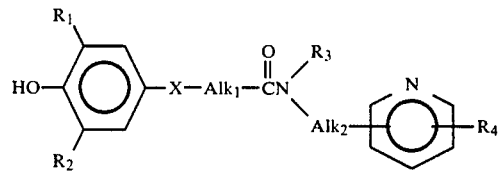

wherein: $R_1$ and $R_2$ are the same or different members of the group consisting of halo, phenyl, phenyl substituted with one or more substituents selected from a group consisting of halo, hydroxy, lower alkyl, lower alkoxy, and a

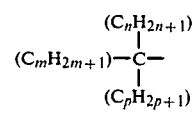

group wherein n, m and p are independently an integer of from 1 to 8 provided $n+m+p$ is equal to or less than 10; X is thio, sulfinyl or sulfonyl; $Alk_1$ is straight or branched chain lower alkylene of 1 to 6 carbon atoms; $R_3$ is lower alkyl; $Alk_2$ is straight or branched chain alkylene of 1 to 4 carbon atoms; $R_4$ is selected from the group consisting of hydrogen, halo, hydroxy, lower alkyl and lower alkoxy; or a pharmaceutically acceptable salt thereof.

2. A compound of claim 1 wherein $R_1$ and $R_2$ each are

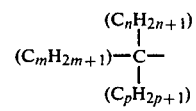

3. A compound of claim 2 wherein $R_1$ and $R_2$ each are 1,1-dimethylethyl.

4. A compound of claim 1 wherein X is thio.

5. A compound of claim 1 wherein X is sulfinyl.

6. A compound of claim 3 wherein X is thio.

7. A compound of claim 6, 3-[[3,5-bis(1,1-dimethylethyl)-4-hydroxyphenyl]thio]-N-methyl-N-[2-(2-pyridinyl)ethyl]propanamide or a pharmaceutically acceptable acid addition salt thereof.

8. A compound of claim 6, 3-[[3,5-bis(1,1-dimethylethyl)-4-hydroxyphenyl]thio]-N-methyl-N-[2-(2-pyridinyl)ethyl]propanamide monohydrochloride.

9. A compound of claim 6, 3-[[3,5-bis(1,1-dimethylethyl)-4-hydroxyphenyl]thio]-N-ethyl-N-(4-pyridinylmethyl)-propanamide or a pharmaceutically acceptable acid addition salt thereof.

10. A compound of claim 6, 3-[[3,5-bis(1,1-dimethylethyl)-4-hydroxyphenyl]thio]-N-methyl-N-[(2-methyl-6-pyridinyl)methyl]propanamide or a pharmaceutically acceptable acid addition salt thereof.

11. A compound of claim 6, 3-[[3,5-bis(1,1-dimethylethyl)-4-hydroxyphenyl]thio]-N-methyl-N-[(2-(4-pyridinyl)ethyl]propanamide or a pharmaceutically acceptable acid addition salt thereof.

12. A compound of claim 1, wherein $R_1$ and $R_2$ each are halo.

13. A compound of claim 12 wherein $R_1$ and $R_2$ each are chloro.

14. A compound of claim 13, 3-[(3,5-dichloro-4-hydroxyphenyl)thio]-N-methyl-[2-(2-pyridinyl)ethyl]propanamide or a pharmaceutically acceptable salt thereof.

15. A compound of claim 1 wherein $R_1$ and $R_2$ each are phenyl or phenyl substituted with one or more substituents selected from a group consisting of halo, hydroxy, lower alkyl and lower alkoxy.

16. A compound of claim 15, 3-[(2'-hydroxy[1,1':3',1''-terphenyl]-5'-yl)thio]-N-methyl-N-[2-(2-pyridinyl)ethyl]propanamide or a pharmaceutically acceptable salt thereof.

17. A pharmaceutical composition for the treatment of inflammation and allergy reactions comprising a therapeutically effective amount of a compound of claim 1 and a pharmaceutically acceptable carrier or diluent.

18. A method of treating inflammation comprising administering a therapeutically effective amount of a compound of claim 1 to a patient in need of such treatment.

19. A method of treating allergic reactions comprising administering a therapeutically effective amount of a compound of claim 1 to a patient in need of such treatment.

* * * * *

UNITED STATES PATENT AND TRADEMARK OFFICE
CERTIFICATE OF CORRECTION

PATENT NO. : 4,663,333

DATED : May 5, 1987

INVENTOR(S) : Mueller, et al.

It is certified that error appears in the above-identified patent and that said Letters Patent is hereby corrected as shown below:

On the front page of the patent where the title of the invention is identified, that part of the title reading "AD USE" should read -- AND USE --.

The above error also occurs on the first line of Column 1 of the patent.

Column 1, lines 10-11, reading "aminoalkylpyridineamides" should read -- acylaminoalkylpyridines --.

Column 13, line 1, reading "EXAMPLE 19" should read -- EXAMPLE 18 --.

Signed and Sealed this

Fourth Day of July, 1989

Attest:

DONALD J. QUIGG

*Attesting Officer*  *Commissioner of Patents and Trademarks*